US012599455B2

(12) United States Patent
Behzadi

(10) Patent No.: US 12,599,455 B2
(45) Date of Patent: Apr. 14, 2026

(54) ELECTRONIC SIGNATURE FOR BONE PREPARATION

(71) Applicant: Kambiz Behzadi, Pleasanton, CA (US)

(72) Inventor: Kambiz Behzadi, Pleasanton, CA (US)

( * ) Notice: Subject to any disclaimer, the term of this patent is extended or adjusted under 35 U.S.C. 154(b) by 131 days.

(21) Appl. No.: 18/405,881

(22) Filed: Jan. 5, 2024

(65) Prior Publication Data

US 2024/0252272 A1 Aug. 1, 2024

Related U.S. Application Data

(60) Provisional application No. 63/528,591, filed on Jul. 24, 2023, provisional application No. 63/481,126, filed on Jan. 23, 2023.

(51) Int. Cl.
| | |
|---|---|
| *A61B 90/00* | (2016.01) |
| *A61B 17/16* | (2006.01) |
| *A61F 2/46* | (2006.01) |
| *G16H 20/40* | (2018.01) |

(52) U.S. Cl.
CPC .......... *A61B 90/06* (2016.02); *A61B 17/1666* (2013.01); *A61F 2/4609* (2013.01); *G16H*

*20/40* (2018.01); *A61B 2090/066* (2016.02); *A61B 2562/0261* (2013.01)

(58) Field of Classification Search
CPC .................................................. A61B 17/1666
See application file for complete search history.

(56) References Cited

U.S. PATENT DOCUMENTS

2017/0196705 A1* 7/2017 Behzadi ................ A61F 2/4607

FOREIGN PATENT DOCUMENTS

GB 2485446 A * 5/2012 .............. H02P 29/02

* cited by examiner

*Primary Examiner* — Andrew Yang
(74) *Attorney, Agent, or Firm* — Patent Law Offices Michael E. WOODS; Michael E. Woods

(57) ABSTRACT

A system and method for a system and method for providing an electronic signature as a method and apparatus for sizing bone for press fit arthroplasty. Electrical signatures of driving motive systems used in bone preparation for the press fit arthroplasty, such as driving motors of reamers and broaches, provide a metric for proper sizing.

8 Claims, 14 Drawing Sheets

Elastic Properties of Rim

Acetabular Rim

1. Apply impact energy E1

2. Measure F2 or F3 over NOITS or and/or ΔF2 or ΔF3 as it approaches zero

3. When ΔF2 or ΔF3 approaches 0, increase E1 to E2

4. Repeat 1-3 until the NOITS required for ΔF2 or ΔF3 to approach 0 reaches threshold minimum value 5. Recommend surgeon discontinue additional force application

1400

1405

1410

1415

1420

ELECTRONIC SIGNATURE FOR BONE PREPARATION

CROSS REFERENCE TO RELATED APPLICATIONS

This application claims the benefit of U.S. Provisional Application 63/528,591 filed on Jul. 24, 2023; and this application claims the benefit of U.S. Provisional Application 63/481,126 filed on Jan. 23, 2023; the contents of which are all hereby expressly incorporated by reference thereto for all purposes.

FIELD OF THE INVENTION

The present invention relates generally to orthopedic surgery, and more specifically, but not exclusively, to press fit arthroplasty.

BACKGROUND OF THE INVENTION

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

Orthopedic surgery involves use of press fit arthroplasty. In this process a bone cavity is prepared smaller, e.g., approximately one mm smaller, than the implant, and the implant is impacted into place with dynamic impacts, for example, use of an orthopedic mallet.

The success of the press fit arthroplasty is dependent on an ability of such an installed implant to obtain primary stability through interference fit. Generally, this means that an implant-bone interface should not allow motion, e.g., beyond 50 μm. When an implant experiences too great of micromotion, such as greater than 50 μm of micromotion, the implant will eventually get loose and fail. Therefore, optimal primary implant stability is critical to the success of press fit arthroplasty.

Three distinct factors affect primary implant stability: (a) press fit process; (b) material properties of the implant (e.g., stiff or flexible); and (c) geometric properties of the implant (e.g., straight, angled). Beyond the material and geometric properties of the implant, the process of press fitting of the implant is crucially important to the success of the implant. The ability to get a good press fit is directly related to the surgeon's ability to properly size the bony cavity for an implant. This is not unlike buying the proper size clothing or footwear: both too tight and too loose are undesirable.

Currently, we have no proper way of sizing the implant beyond surgeon's visual assessment of templates on preoperative X-rays, and the reliance on the surgeon's visual, tactile, and auditory senses intra-op, during the bone preparation process (reaming and broaching). These techniques are individually and collectively qualitative in nature and therefore are non-standardized with complete reliance on the surgeon's personal experience, and to some extent, the surgeon's and patient's luck.

BRIEF SUMMARY OF THE INVENTION

Disclosed is a system and method for providing an electronic signature as a method and apparatus for sizing bone for press fit arthroplasty. Electrical signatures of driving motive systems used in bone preparation for the press fit arthroplasty, such as driving motors of reamers and broaches, provide a metric for proper sizing.

The following summary of the invention is provided to facilitate an understanding of some of the technical features related to using electrical signatures of bone preparation motive systems, and is not intended to be a full description of the present invention. A full appreciation of the various aspects of the invention can be gained by taking the entire specification, claims, drawings, and abstract as a whole. The present invention is applicable to other bone preparation systems and methods used for press fit arthroplasty.

An embodiment of the present invention includes use of electrical/electronic signatures of motive systems and/or force/torque sensors used in operating bone preparation implements for press fit arthroplasty installing an implant in prepared bone.

An embodiment of the present invention includes monitoring these electrical/electronic signatures during bone preparation for a characteristic indicating that the prepared bone is near or at an elastic limit.

Any of the embodiments described herein may be used alone or together with one another in any combination. Inventions encompassed within this specification may also include embodiments that are only partially mentioned or alluded to or are not mentioned or alluded to at all in this brief summary or in the abstract. Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

Other features, benefits, and advantages of the present invention will be apparent upon a review of the present disclosure, including the specification, drawings, and claims.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION OF THE INVENTION

Figure 1:
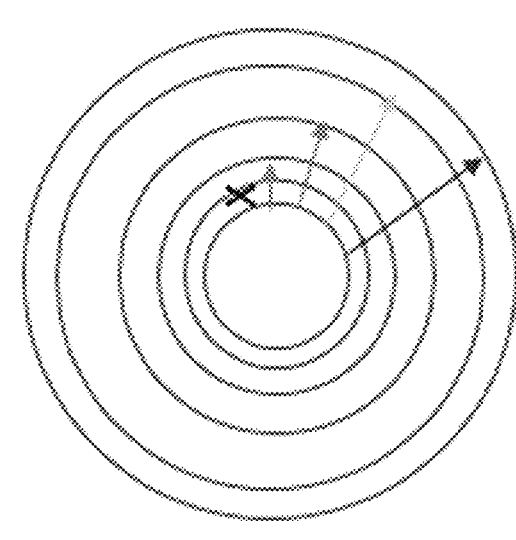
FIG. 1 illustrates an acetabular ring model.
Figure 1:
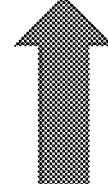
Figure 1:
Figure 1:
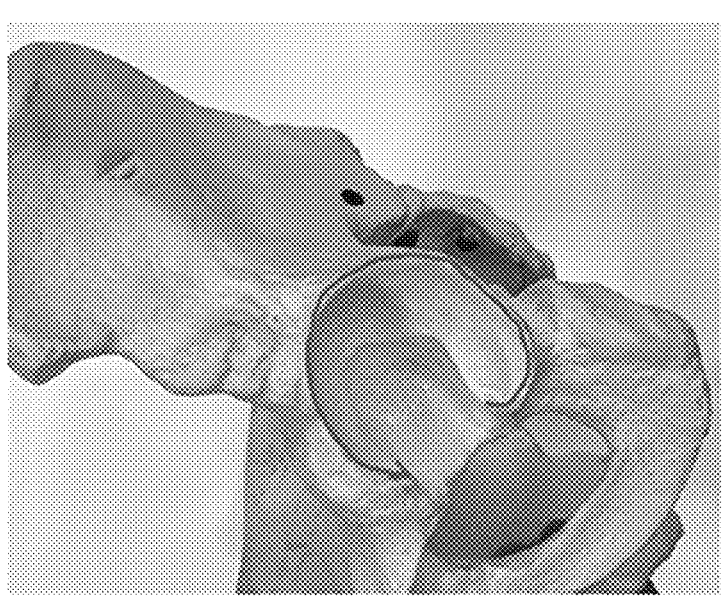

Embodiments of the present invention provide a system and method for an electronic signature as a method and apparatus for sizing bone for press fit arthroplasty. The following description is presented to enable one of ordinary skill in the art to make and use the invention and is provided in the context of a patent application and its requirements.

Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

Definitions

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The following definitions apply to some of the aspects described with respect to some embodiments of the invention. These definitions may likewise be expanded upon herein.

As used herein, the term "or" includes "and/or" and the term "and/or" includes any and all combinations of one or more of the associated listed items. Expressions such as "at least one of," when preceding a list of elements, modify the entire list of elements and do not modify the individual elements of the list.

As used herein, the singular terms "a," "an," and "the" include plural referents unless the context clearly dictates otherwise. Thus, for example, reference to an object can include multiple objects unless the context clearly dictates otherwise.

Also, as used in the description herein and throughout the claims that follow, the meaning of "in" includes "in" and "on" unless the context clearly dictates otherwise. It will be understood that when an element is referred to as being "on" another element, it can be directly on the other element or intervening elements may be present therebetween. In contrast, when an element is referred to as being "directly on" another element, there are no intervening elements present.

As used herein, the term "set" refers to a collection of one or more objects. Thus, for example, a set of objects can include a single object or multiple objects. Objects of a set also can be referred to as members of the set. Objects of a set can be the same or different. In some instances, objects of a set can share one or more common properties.

As used herein, the term "adjacent" refers to being near or adjoining. Adjacent objects can be spaced apart from one another or can be in actual or direct contact with one another. In some instances, adjacent objects can be coupled to one another or can be formed integrally with one another.

As used herein, the terms "connect," "connected," and "connecting" refer to a direct attachment or link. Connected objects have no or no substantial intermediary object or set of objects, as the context indicates.

As used herein, the terms "couple," "coupled," and "coupling" refer to an operational connection or linking. Coupled objects can be directly connected to one another or can be indirectly connected to one another, such as via an intermediary set of objects.

The use of the term "about" applies to all numeric values, whether or not explicitly indicated. This term generally refers to a range of numbers that one of ordinary skill in the art would consider as a reasonable amount of deviation to the recited numeric values (i.e., having the equivalent function or result). For example, this term can be construed as including a deviation of ±10 percent of the given numeric value provided such a deviation does not alter the end function or result of the value. Therefore, a value of about 1% can be construed to be a range from 0.9% to 1.1%.

As used herein, the terms "substantially" and "substantial" refer to a considerable degree or extent. When used in conjunction with an event or circumstance, the terms can refer to instances in which the event or circumstance occurs precisely as well as instances in which the event or circumstance occurs to a close approximation, such as accounting for typical tolerance levels or variability of the embodiments described herein.

As used herein, the terms "optional" and "optionally" mean that the subsequently described event or circumstance may or may not occur and that the description includes instances where the event or circumstance occurs and instances in which it does not.

As used herein, the term "size" refers to a characteristic dimension of an object. Thus, for example, a size of an object that is spherical can refer to a diameter of the object. In the case of an object that is non-spherical, a size of the non-spherical object can refer to a diameter of a corresponding spherical object, where the corresponding spherical object exhibits or has a particular set of derivable or measurable properties that are substantially the same as those of the non-spherical object. Thus, for example, a size of a non-spherical object can refer to a diameter of a corresponding spherical object that exhibits light scattering or other properties that are substantially the same as those of the non-spherical object. Alternatively, or in conjunction, a size of a non-spherical object can refer to an average of various orthogonal dimensions of the object. Thus, for example, a size of an object that is a spheroidal can refer to an average of a major axis and a minor axis of the object. When referring to a set of objects as having a particular size, it is contemplated that the objects can have a distribution of sizes around the particular size. Thus, as used herein, a size of a set of objects can refer to a typical size of a distribution of sizes, such as an average size, a median size, or a peak size.

Orthopedic surgery involves use of press fit arthroplasty. In this process the bone cavity is prepared approximately 1 mm smaller than the implant, and the implant is impacted into place with dynamic impacts.

The success of the press fit arthroplasty is dependent on the ability of the implant to obtain primary stability through interference fit. Generally, this means that implant bone interface should not allow motion beyond 50 μm. If the implant experiences greater than 50 μm of micromotion, the implant will eventually get loose and fail. Therefore, optimal primary implant stability is critical to the success of press fit arthroplasty.

Three distinct factors affect primary implant stability: 1. Press fit process 2. Material properties of the implant (stiff or flexible) 3. Geometric properties of the implant (straight, angled). Beyond the material and geometric properties of the implant, the process of press fitting of the implant is crucially important to the success of the implant. The ability to get a good press fit is directly related to the surgeon's ability to properly size the bony cavity for an implant. This is not unlike buying the proper size Jeans or shoes. Too tight is as bad as too loose.

Currently, we have no proper way of sizing the implant beyond surgeon's visual assessment of templates on pre-operative X-rays, and the reliance on the surgeon's visual, tactile, and auditory senses intra-op, during the bone preparation process (reaming and broaching). These techniques are individually and collectively qualitative in nature and therefore are non-standardized with complete reliance on the surgeon's personal experience.

The sizing of the implant is basically a simple Newtonian problem. How much should we stretch the bone to get the best elasticity or grasping force at the rim, without causing fracture.

FIG. 1 illustrates an acetabular ring model. Current practice of bone preparation involves reaming the acetabulum to a bleeding surface; or broaching the femur until a firm tactile fit is felt, along with a change in pitch. Frequently, the surgeon has no idea how much to ream or to broach the bone. After the reaming is complete for example, the acetabular bone may show partially subcortical and partially trabecular bone. Should the surgeon remove all the dense subcortical bone? The current art is a non-standardized and qualitative process. Each surgeon does her own technique of reaming and broaching with her own rational, using her own visual, auditory, and tactile senses along with her experience as a guide.

In truth, there is no process of sizing bone in orthopedic arthroplasty. Surgeons prepare bone based on the personal technique and then impact a prosthesis into position.

Typically, a prosthesis, usually 1 mm larger in diameter than the prepared bony cavity is impacted into place. For example, the acetabulum may be reamed to 55 mm and then a 56 mm cup is implanted (impacted). It is also well known that the numerical representation of the size of the implant as reported by the medical device companies is not truly accurate. Most implants are usually about 0.7 mm or 0.5 mm larger than what is stated on the implant. Therefore, a 56 mm cup may truly be a 56.5 mm cup. This appears to be standard practice for both acetabular cups and femoral stems.

One fundamental problem in current press fit arthroplasty techniques is that preparation of the bone is NOT the same as sizing of the bone. We believe that the process of press fit arthroplasty should include 1. Preparation. 2. Sizing 3. Implantation. Current techniques do not involve a sizing process (step 2).

Assuming an experienced surgeon has a good feel for how much to ream and or broach, this still does not solve the problem that hip replacements around the globe are being done based on different individual techniques that are qualitative based on personal experience. This concern is significant because most (80%) total hip replacements are done by surgeons who do less than 10 THRs per year. The younger and inexperienced surgeons will never be able to get the experience they need to obtain the proper feel on how to prepare bone properly for press fit arthroplasty.

The obvious problem in current art is that the preparation of the bone, whether it is reaming of the acetabulum or broaching of the femur, is a qualitative process. The surgeon looks for bleeding bone (blush), listens for change in pitch and feels for a change in tactile sensation in the reamer or broach. This qualitative process is extremely inaccurate in determining the implant/bone (I/B) contact condition.

Too much I/B contact leads to fracture. Too little I/B contact leads to loosening. Surgeons want the highest I/B contact that provides optimum primary implant stability (best press fit). However, surgeons do not want to risk fracture and or severe damage to bone.

Figure 2:
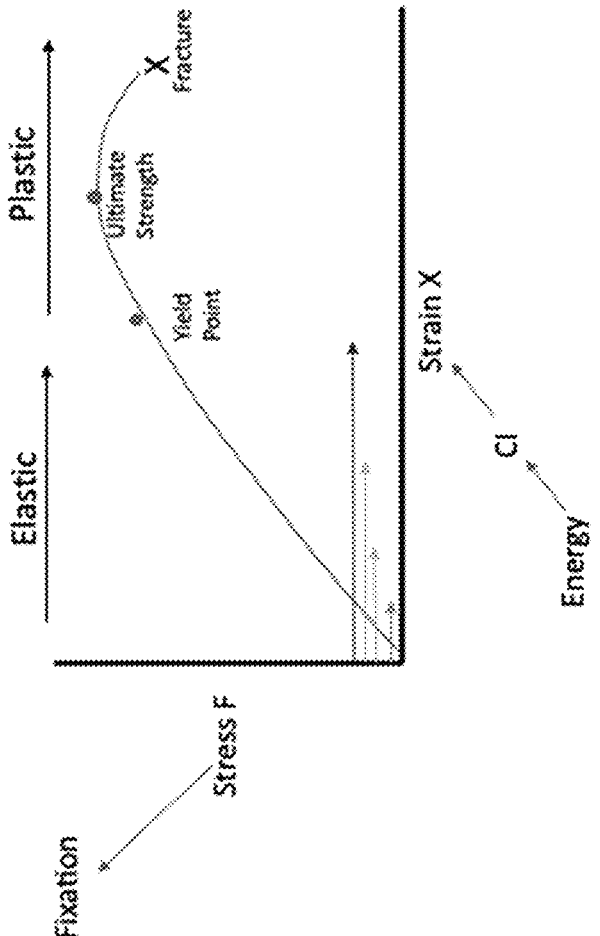
FIG. 2 illustrates a set of considerations when calibrating an acetabular ring.
Figure 2:
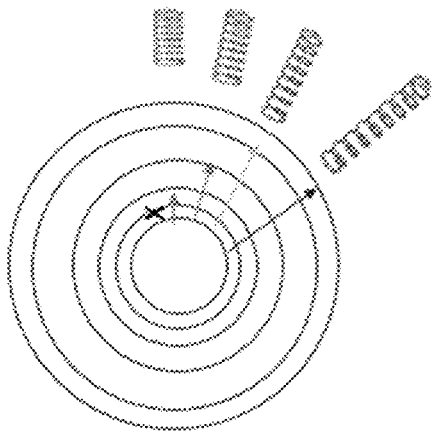

Ultimately the surgeon is seeking a high implant bone contact force to assure a good interference fit. However, this is a goldilocks problem. Bone behaves like a stiff circular composite spring. FIG. 2 illustrates a set of considerations when calibrating an acetabular ring.

Proper press fit is usually in the range of 0.5 mm to 1.0 mm. If the surgeon over reams or over broaches, the implant will get loose or subside. If the surgeon under reams or under broaches, and then uses excessive force to implant the implant, she may damage osteocytes and vascularity of bone, create an occult fracture where all elasticity is lost, or create a frank fracture of the bone.

There is a need for a better solution in sizing the bony cavities for press fit fixation. We have previously described the best fixation short of fracture BFSF fixation algorithm that helps the surgeon know how hard to impact and when to stop impacting during a press fit process. This fixation is accomplished by directly measuring forces in bone, impactors, and impaction rods. Inputting these values into the BFSF fixation algorithm, which then determines how much force to methodically apply and when to stop impaction. The BFSF algorithm determines whether to increase force and whether to stop impacting based on a computational analysis of forces experienced in the bone, the impaction rod and the impacting tool.

The BFSF feedback algorithm also applies to cutting tools such as broaches. A "rate of insertion factor" is a representation of an elastic limit of bone. Slow rate of insertion suggests that there is significant elasticity left in the bony cavity. High rate of insertion suggests that there is very little elasticity left in the bony cavity.

Figure 3:
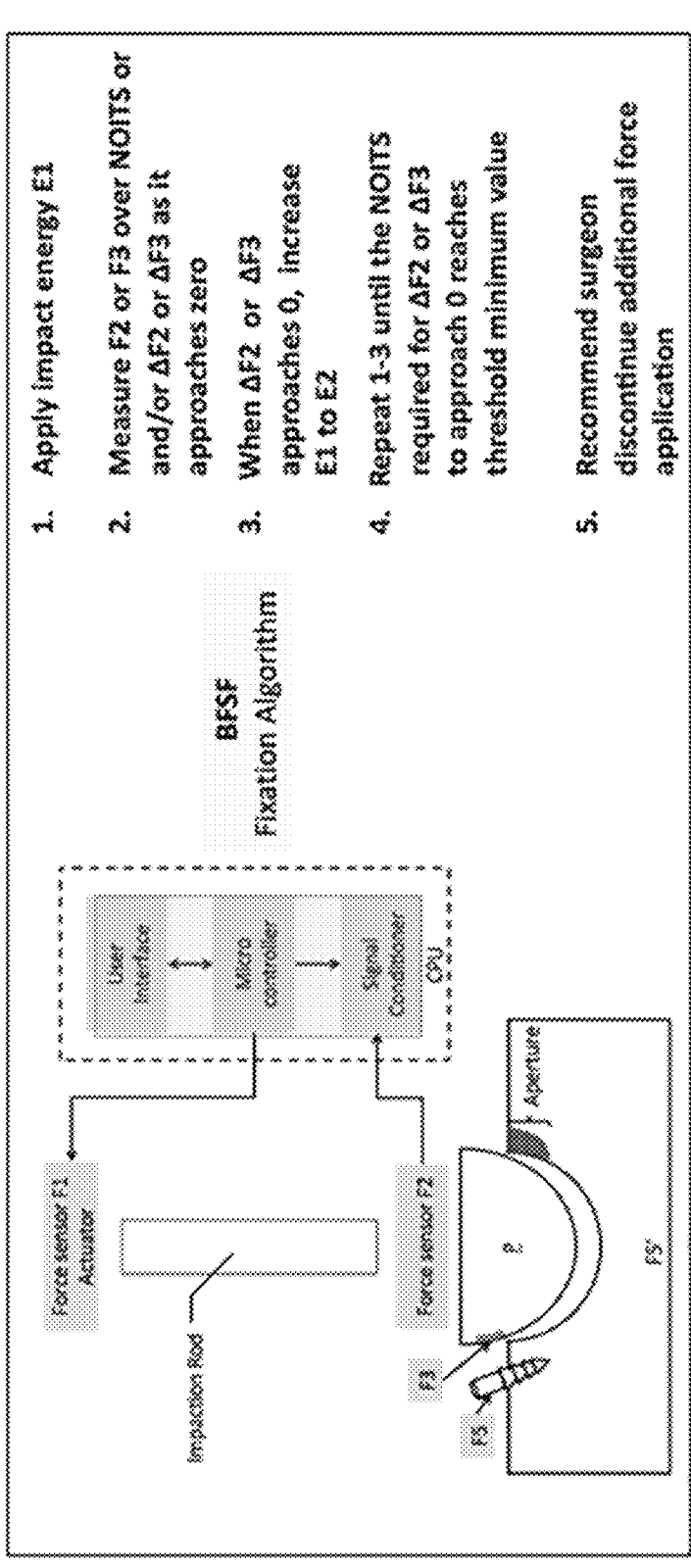
FIG. 3 illustrates a force feedback mechanism.

FIG. 3 illustrates a force feedback mechanism. However, this process assumes that the bony cavity is properly sized. Orthopedic surgeons do not have a quantitative method to properly size bony cavities, including bones like the acetabulum, proximal femur, proximal humerus, and various other bones. As noted earlier, the surgeon sizes bony cavities qualitatively based on their own personal experience. There is no standardized process for sizing the bony cavities for press fit fixation in orthopedics.

Since the surgeon decides how much to ream and how much to broach based on her visual, tactile, and auditory senses, the bony cavity may be properly sized, under-sized or over-sized.

This phenomenon typically creates insecurity in the orthopedic surgeon's world. As an example, surgeon A, after having done twenty total hip replacements, may fracture the acetabulum in the reaming and impaction process. This surgeon may have underreamed the acetabulum and impacted too large a cup, which fractured the acetabulum. This surgeon may likely change her practice in the future and tend over ream the acetabulum, impact smaller cups, and additionally start to use screws to augment fixation.

Alternatively, surgeon B, after having done twenty total hip replacements may see one of his patients show up with a loose acetabular component. The surgeon may have over-reamed the acetabulum and impacted too small a cup. In the future, this surgeon will then tend to under ream the acetabulum and impact oversized cups. That is until he fractures the acetabulum, and the pendulum swings the other way, and this process is repeated all over again.

There is a need for a quantitative process for sizing bony cavities for press fit fixation. There is a need for a quantitative process to assess the Implant/Bone contact condition.

Total Hip Replacements (THR) serves as an example of all press fit arthroplasty in orthopedics. In hip replacements oversized implants are impacted into undersized cavities to obtain interference fit fixation.

The mechanical points of interest in acetabular and femoral fixation in primary hip replacements (as opposed to revision hip replacements) focus on the rim of the acetabulum and the proximal aspect of the femur. With respect to proximal femur, specifically the dense cortical bone of the medial calcar bears a significant part of the load.

Figure 4:
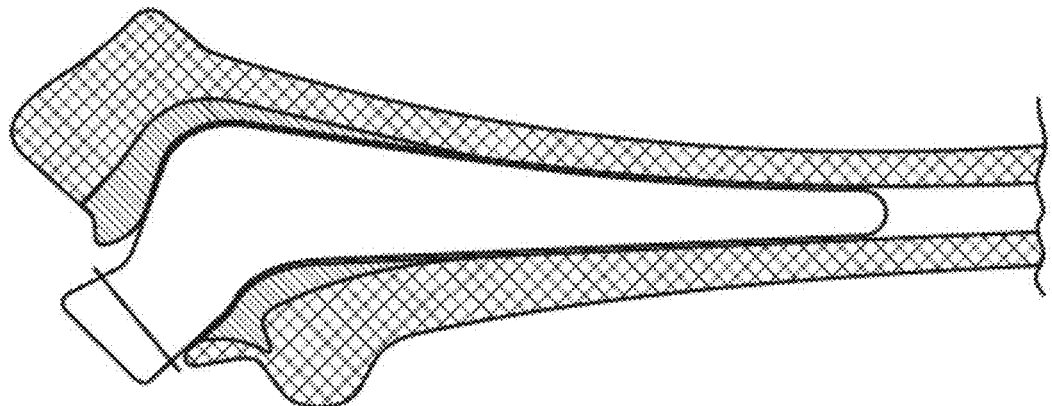
FIG. 4 illustrates contact conditions of prepared bone at a bone-implant interface for both an acetabular cup and a femur implant.
Figure 4:
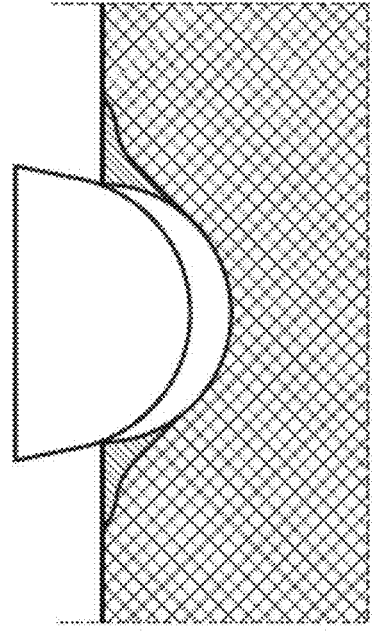

FIG. 4 illustrates contact conditions of prepared bone at a bone-implant interface for both an acetabular cup and a femur implant—with highlighted/emphasized regions of the bone contacting the preparation implement (reamer/broach for example)—illustrating the contact areas of consideration.

To monitor the contact conditions between the bone and implant in arthroplasty, direct measurement methods have been tried, including measuring force at the level of bone and implant, with a variety of force sensors and accelerometers. However, these methods are difficult and expensive to implement in the OR.

Indirect methods of measuring force, and torque, which represent contact conditions between the implant and bone, can also be obtained by using dynamometers with load cells that can provide a measure of the sensed strain in the system, in terms of electrical charge and electrical resistance. However, use of multi-component dynamometers is very expensive, adds bulk to the surgical tools, and not practical. This method may become more practical as dynamometers become more available in smaller sizes.

Another indirect method of monitoring frictional force and torque, as a representation of contact conditions between implant and bone, is to use electronic signatures of driving motors. The transient electric power and electric current of the driving motors used in tools to ream and/or broach the acetabular and femoral bones can provide a reliable estimate of actual measured frictional force and torque sensed at the implant bone I/B interface, and therefore can provide an accurate representation of the I/B contact condition.

Figure 5:
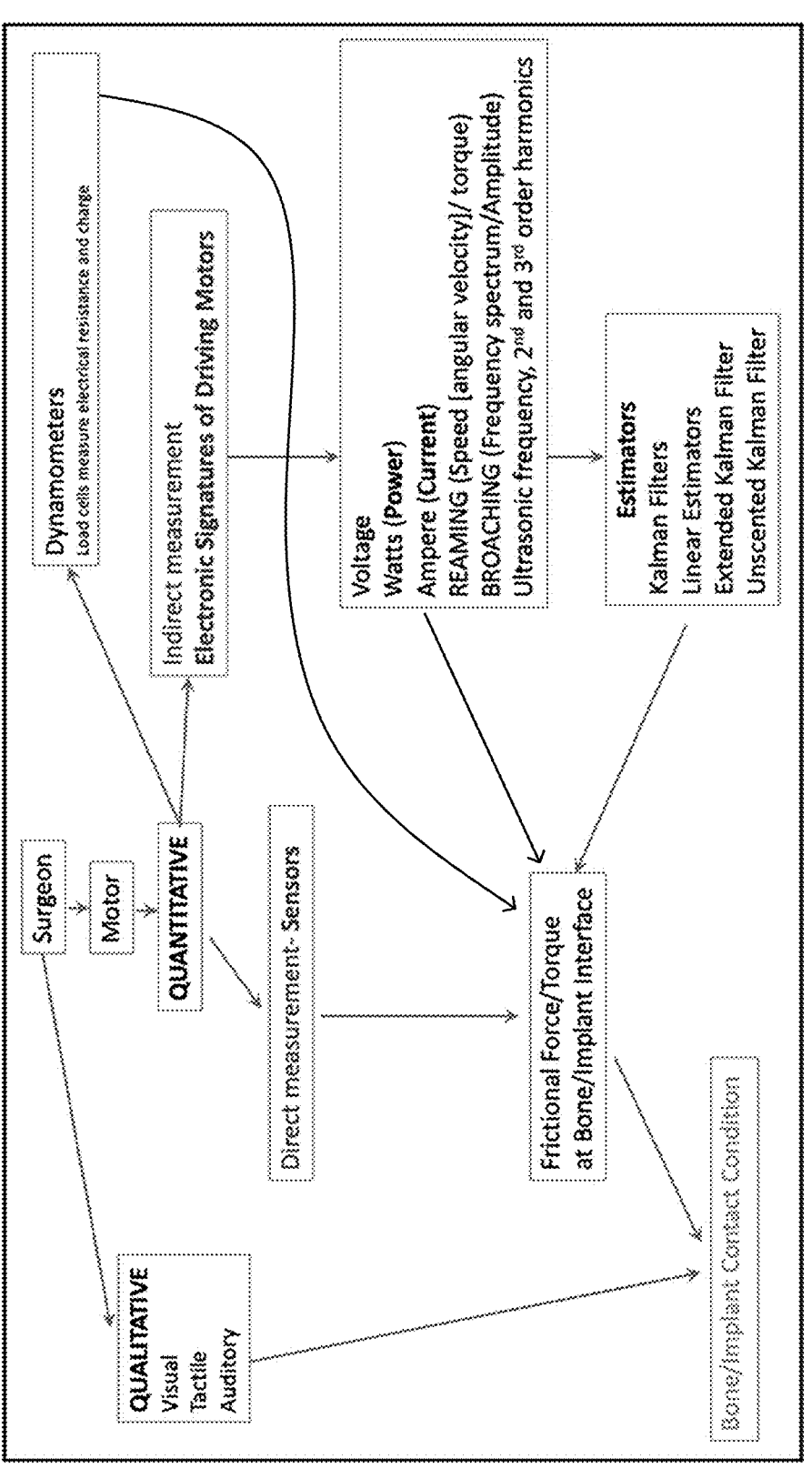
FIG. 5 illustrates a set of force monitoring techniques, including direct and indirect techniques, and qualitative and quantitative techniques.

FIG. 5 illustrates a set of force monitoring techniques, including direct and indirect techniques, and qualitative and quantitative techniques.

Frictional force and torque can be measured from the input electrical power and current of the motor driving reamers and the broaches. The frictional force and torque estimated in this fashion can provide a quantitative measurement of the implant/bone contact condition. This estimated value of frictional force can be shown to the surgeon in digital or numerical form providing guidance as to when reaming and or broaching should stop to prevent irreparable damage to the bone. In this manner the surgeon can quantitatively assess the Newtonian limit of the bony cavity, without having to rely on her own senses.

Figure 6:
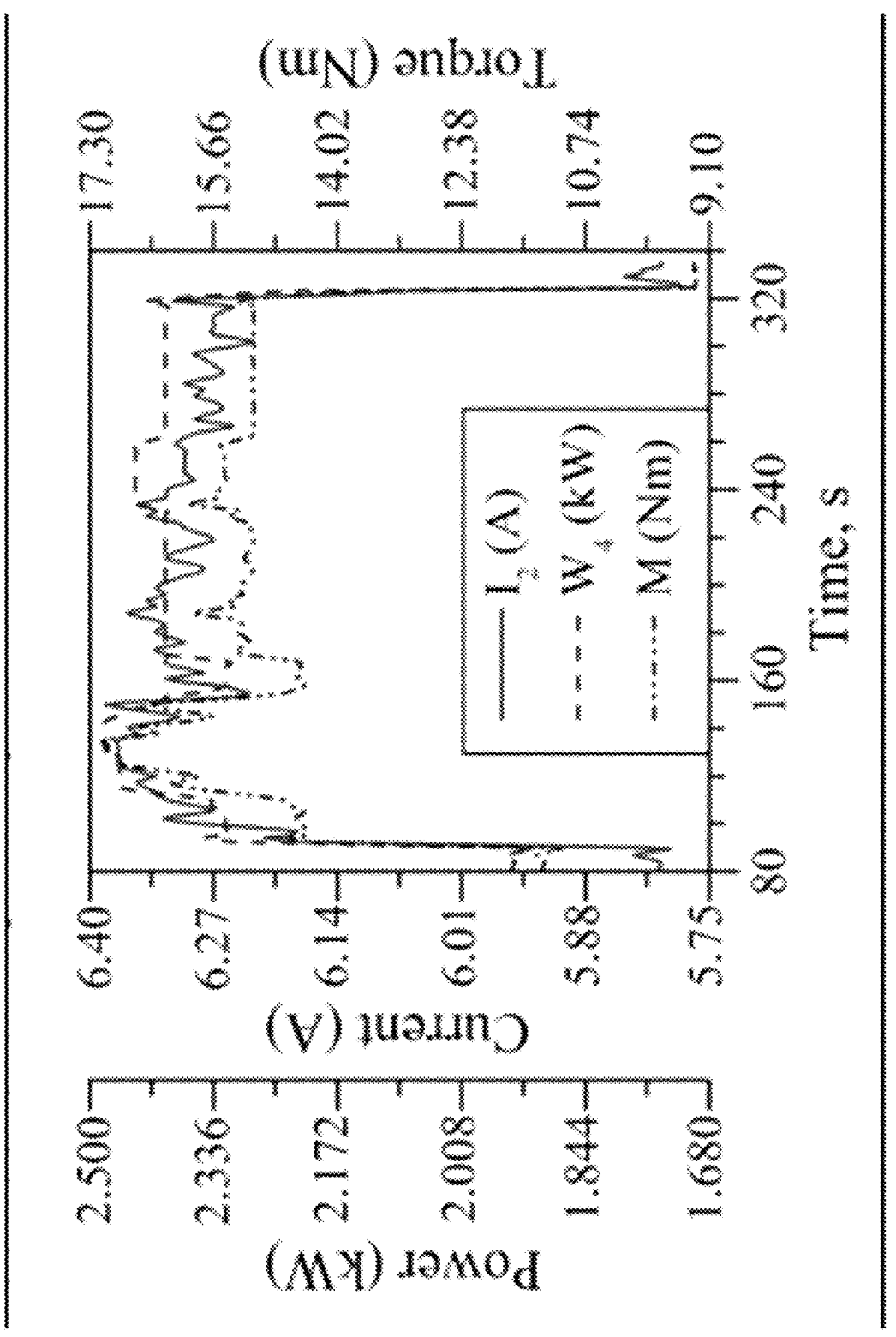
FIG. 6 illustrates a quantitative measurement of implant/bone contact conditions by measurement of input electric power and current of an electric motor used in driving a reamer or a broach during bone preparation for press fit fixation.

FIG. 6 illustrates a quantitative measurement of implant/bone contact conditions by measurement of input electric power and current of an electric motor used in driving a reamer or a broach during bone preparation for press fit fixation.

Furthermore, Estimation Theory concepts such as Kalman Filter, Extended Kalman Filter and Unscented Kalman Filter can be utilized to optimize the values of frictional force and torque, further enhancing the quality of the estimates of the implant bone contact condition.

Figure 7:
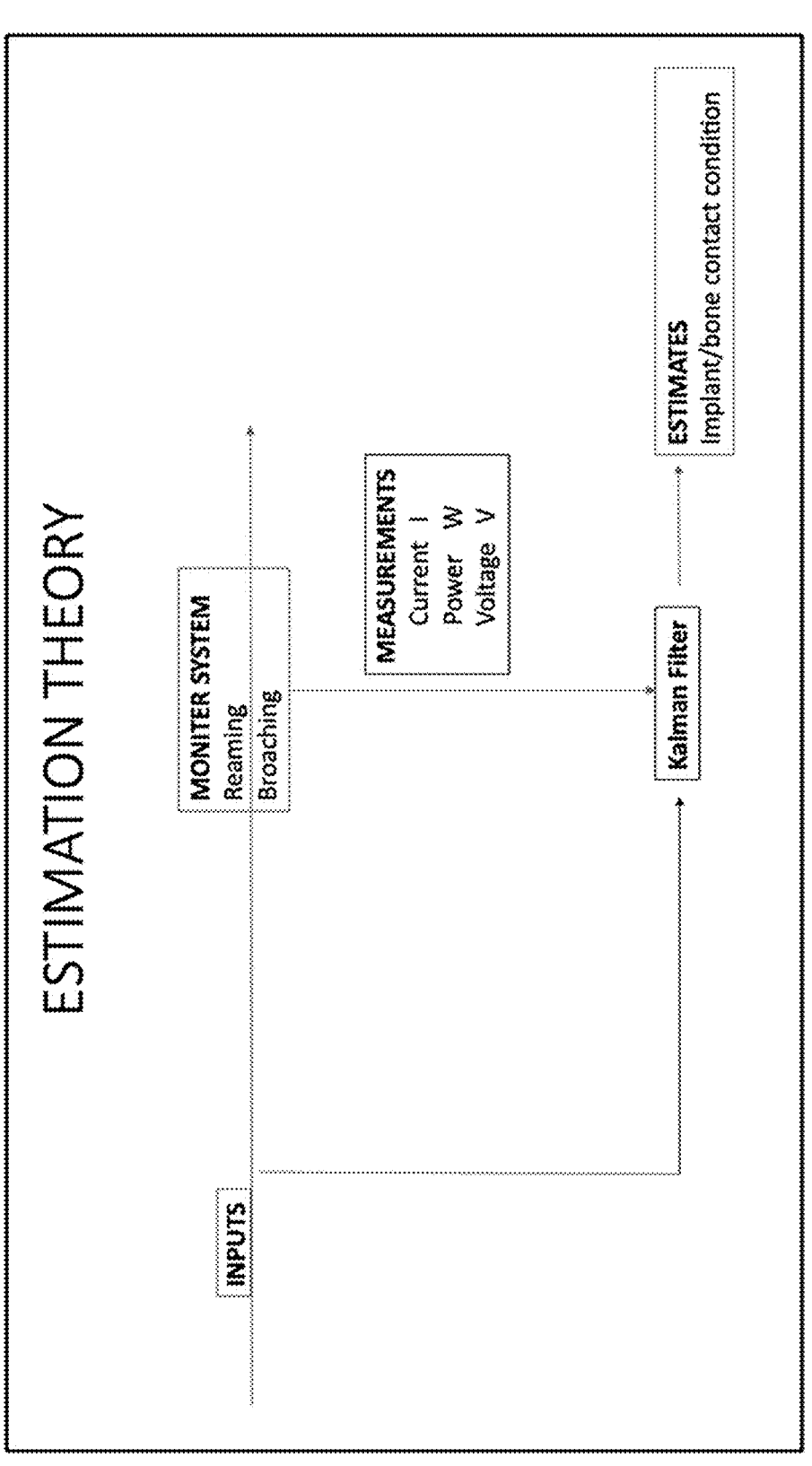
FIG. 7 illustrates an estimation theory that may be used to optimize frictional force and torque.

FIG. 7 illustrates an estimation theory that may be used to optimize frictional force and torque.

The Implant/Bone interface basically acts as a variable rheostat causing decrease or increase in current and power consumption within the system. At certain stage during the reaming and broaching process, as the frictional forces and torque increase, current and power consumption will reach an inflection point/limit which suggests that the elastic limit of the bone has been reached and therefore reaming/broaching should stop. This state may be represented by the changes in current, power, active power, voltage, speed (angular velocity), torque, amplitude, and frequency. When ultrasonic energy is used the change may be represented in the harmonics, specifically 2nd and 3rd order harmonics.

Figure 8:
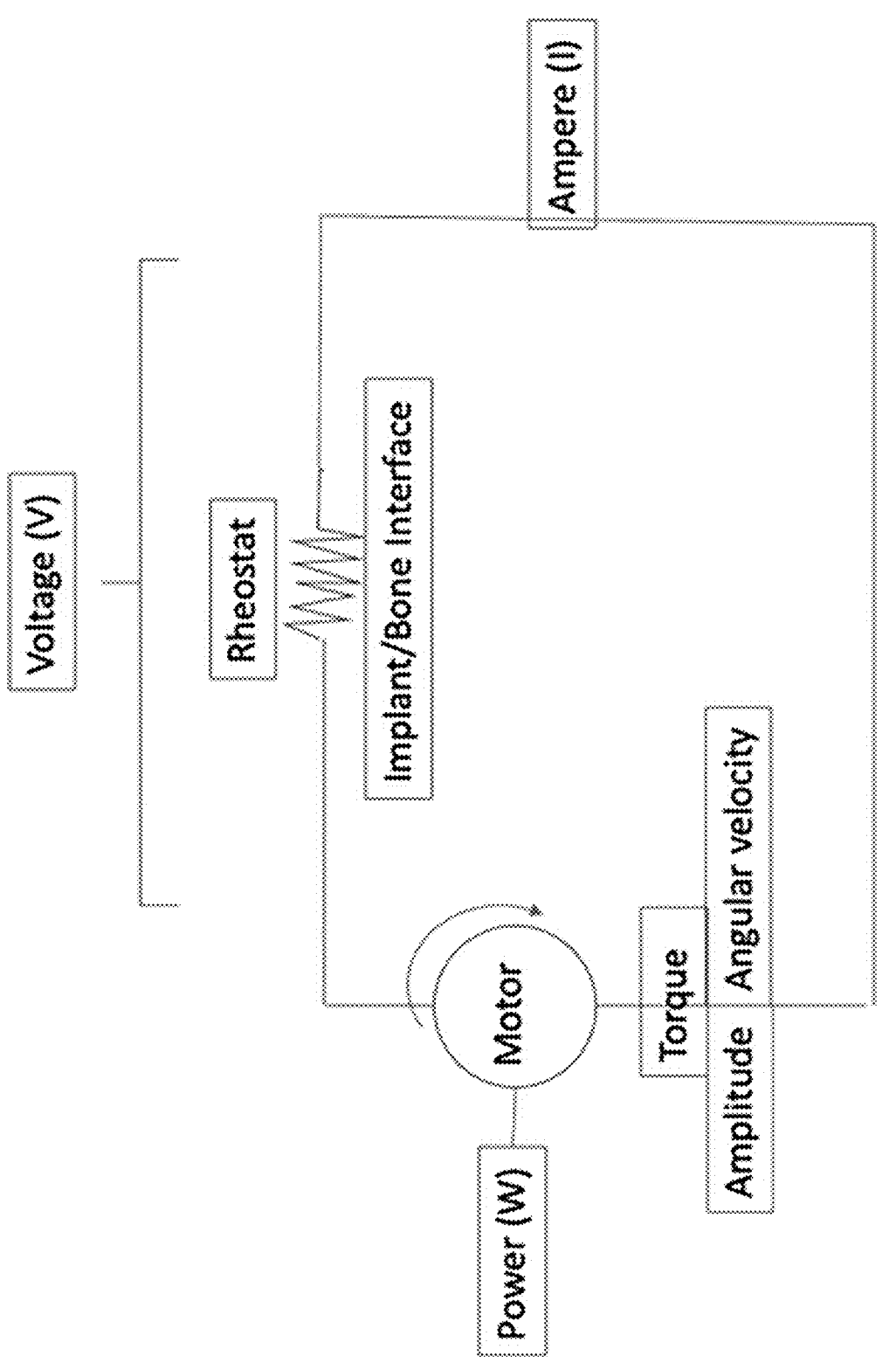
FIG. 8 illustrates use of an implant/bone interface as a variable rheostat in a rotating reamer preparation tool for developing an electrical signature.
Figure 9:
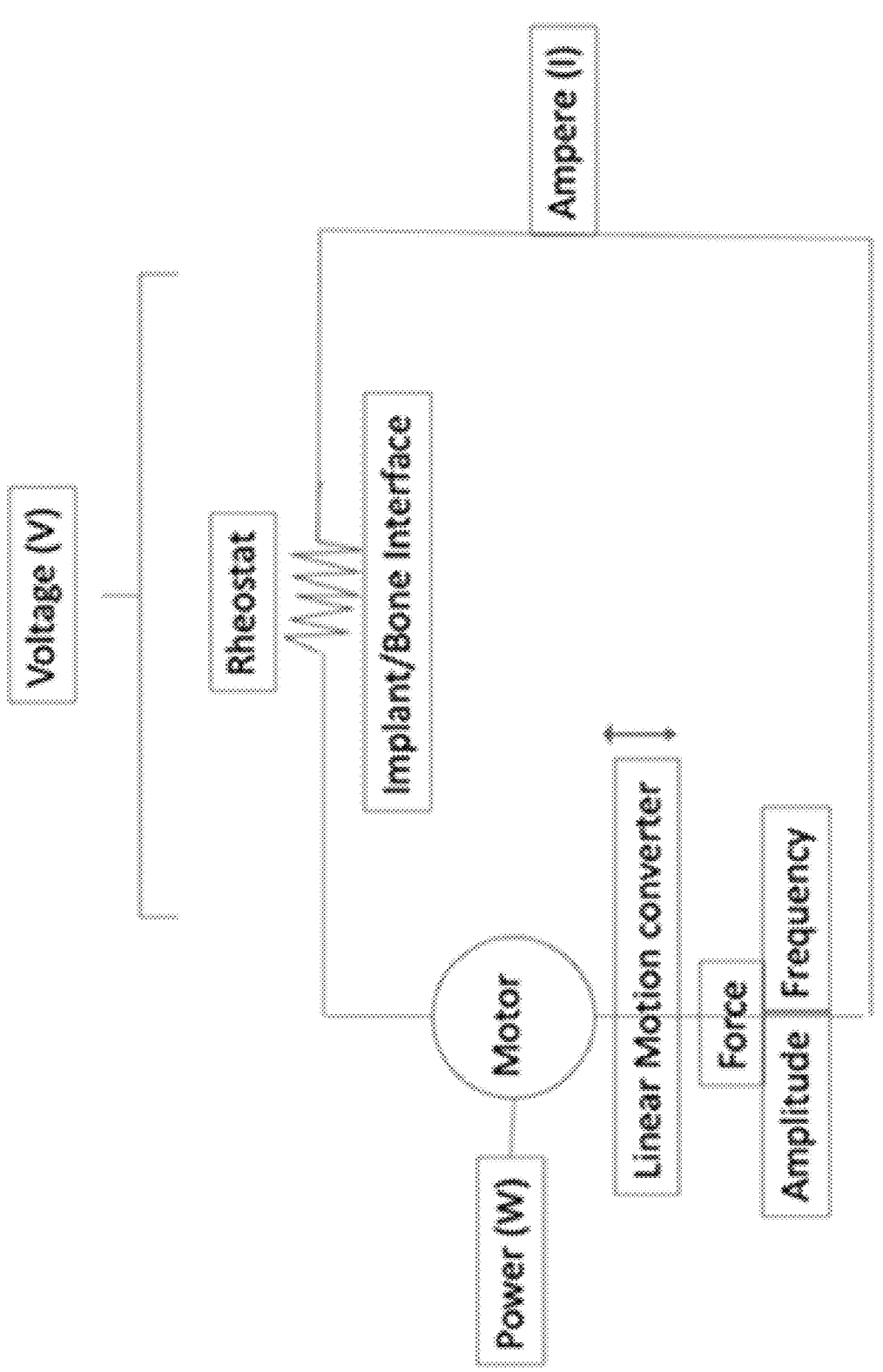
FIG. 9 illustrates use of an implant/bone interface as a variable rheostat in a vibrating broach preparation tool for developing an electrical signature.
Figure 10:
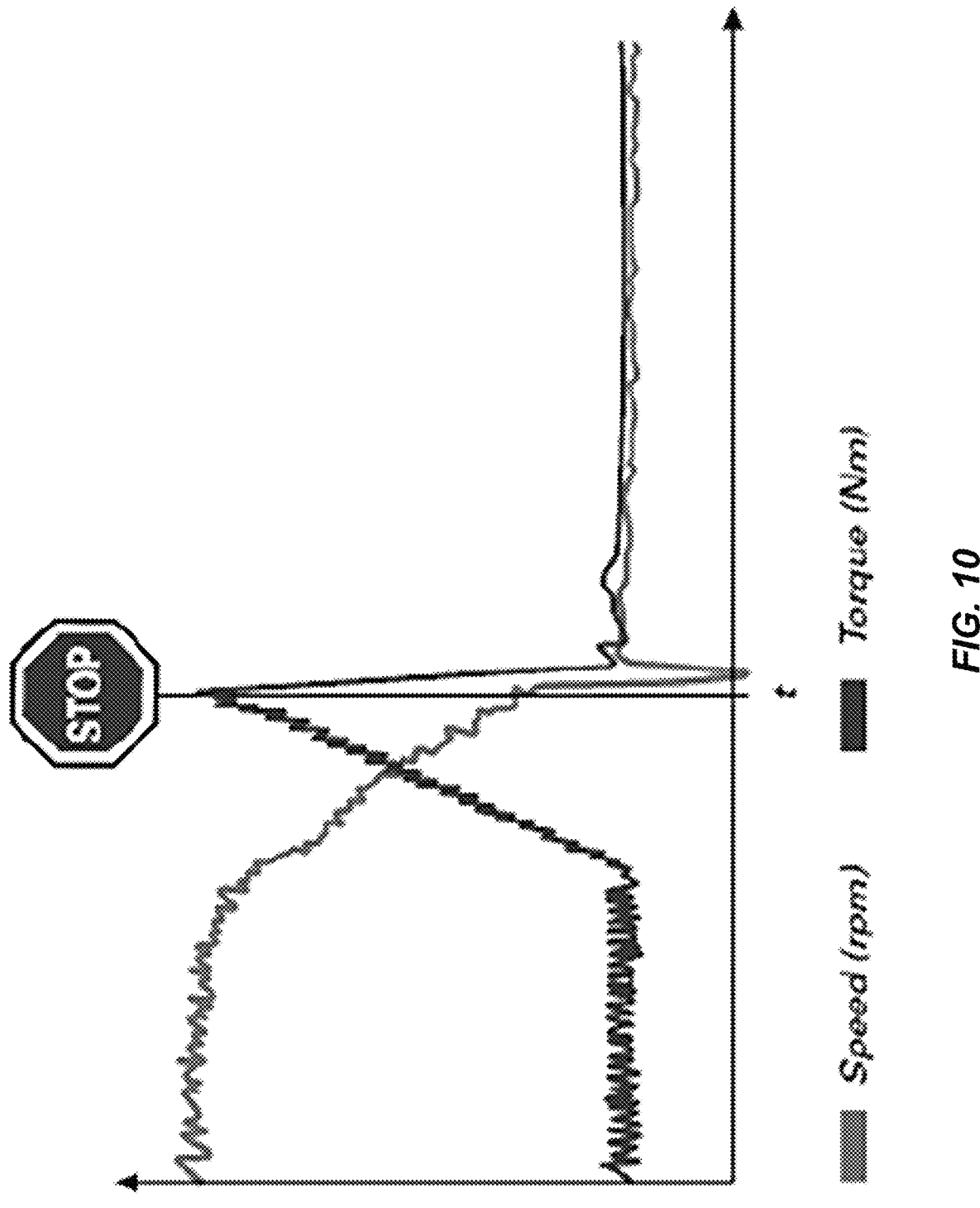
FIG. 10 illustrates an example of use of an inflection point for a bone preparation tool such as those of FIG. 9 and FIG. 10 representing preparation at or near an elastic limit of the bone being prepared.

FIG. 8 illustrates use of an implant/bone interface as a variable rheostat in a rotating reamer preparation tool for developing an electrical signature; FIG. 9 illustrates use of an implant/bone interface as a variable rheostat in a vibrating broach preparation tool for developing an electrical signature; and FIG. 10 illustrates an example of use of an inflection point for a bone preparation tool such as those of FIG. 9 and FIG. 10 representing preparation at or near an elastic limit of the bone being prepared.

The process of monitoring of the implant/bone conditions by monitoring the electrical signatures of the driving motors of the broaches and reamers that cut bone is a novel concept.

It can: 1. Provide a new method of sizing bony cavities for press fit fixation in orthopedic arthroplasty procedures and 2. Provide a standardization process for press fitting of orthopedic implants.

The benefits include decreased morbidity, fewer complications, less revision surgery for patients. Decreased stress for surgeons. Tens of billions of dollars in savings for Medicare and private payers from better/fewer revisions.

Another indirect method is described below. Force/Torque (F/T) sensors may have application in tactile force sensing of an elastic limit of bone. A way to obtain a quantitative measurement of the mechanical stress response of bone along with its physical size during the bone preparation process is with the use dynamometers, force gauges, and force/torque sensors. Dynamometers measure force, torque, power, and rotational speed of an engine. Basic dynamometers can be of two types: power absorption and power transmission. Power absorption dynamometers measure the output of absorbed power. Power transmission dynamometers have a set of strain gauges that measure the strain of an object. The strain gauges are placed along a moving motor shaft/wheel, and torque is measured by the angular deformation of the motor shaft. Dynamometers can be used to directly measure force experienced at the bone-implant interface.

Force/Torque sensors may use a variety of strain gauges such as silicon strain gauges that convert mechanical loads into force/torque measures simultaneously in all of six degrees of freedom (multi-axis force/torque transducer). In the case of an orthopedic bone resecting instrument such as a reamer or a broach, the sensing structure can be the actual cutting surface of the reamer or broach.

Figure 11:
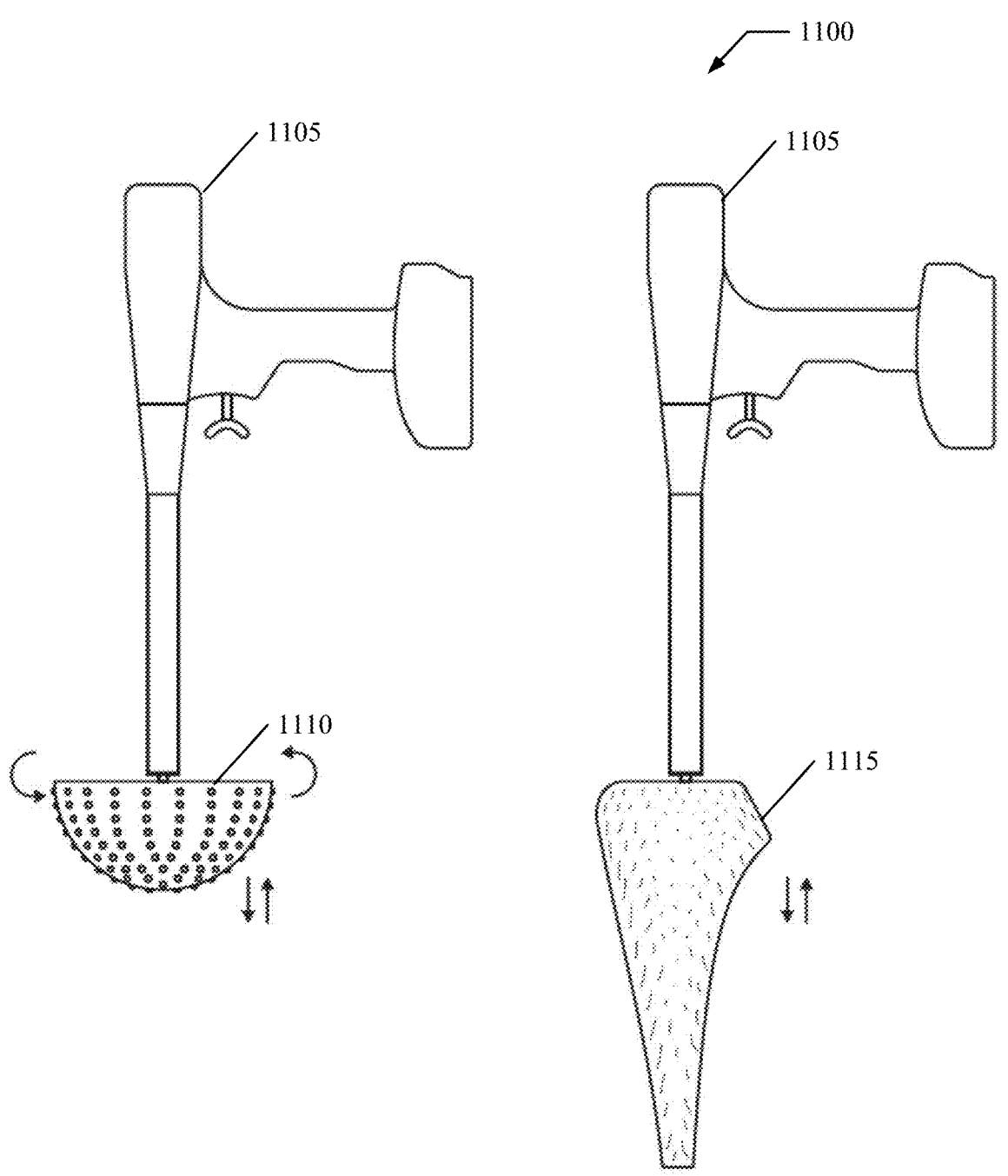
FIG. 11 illustrates a pair of tools that may include embodiments of the present invention, for example, an acetabular reamer/broach and a femoral broach.

FIG. 11 illustrates a pair of tools 100 that may include embodiments of the present invention, for example, an acetabular reamer/broach and a femoral broach. The acetabular broach includes a driver 1105 (a representative driver is depicted which may impart rotary and/or reciprocating motion of a shaft upon which a bone preparation tool is affixed.) The acetabular reamer includes an acetabular reamer/broach 1110 affixed to the shaft. When the shaft rotates, the bone preparation tool operates as a reamer. When the shaft reciprocates, the bone preparation tool operates as a broach. The tool may perform one or both functions, and in some cases the functions may be concurrently provided.

For the femoral broach, a femoral broach bone preparation tool 1115 is affixed to the shaft of driver 1105. In this broach mode, driver 1105 operates the shaft in only reciprocating mode.

With respect to bone resection and force sensing of the elastic limit of bone. The resecting surface of a reamer or broach that comes into contact with bone becomes the actual sensing structure. In one exemplary form the cutting surface is housed in an outer wall and is connected to an inner hull with spokes or sensing beams and flexures that have force strain gauges, such as silicon force strain gauges. These force gauges function as transducers, the output of which is six channels of strain gauge voltages. This output is digitized and converted into Force and Torque through a matrix calculation.

A benefit of the force/torque sensor over a single load cell is that it provides a complete picture of all the forces acting on the transducer, instead of just one snapshot of a single force measurement in a single axis.

This system includes a transducer, high flex-cable, and an intelligent data acquisition system, Ethernet/DeviceNet interface or F/T controller. F/T sensors have application in bone resection by providing a quantitative tactile sense of the frictional and radial forces at the bone implant interface.

Figure 12:
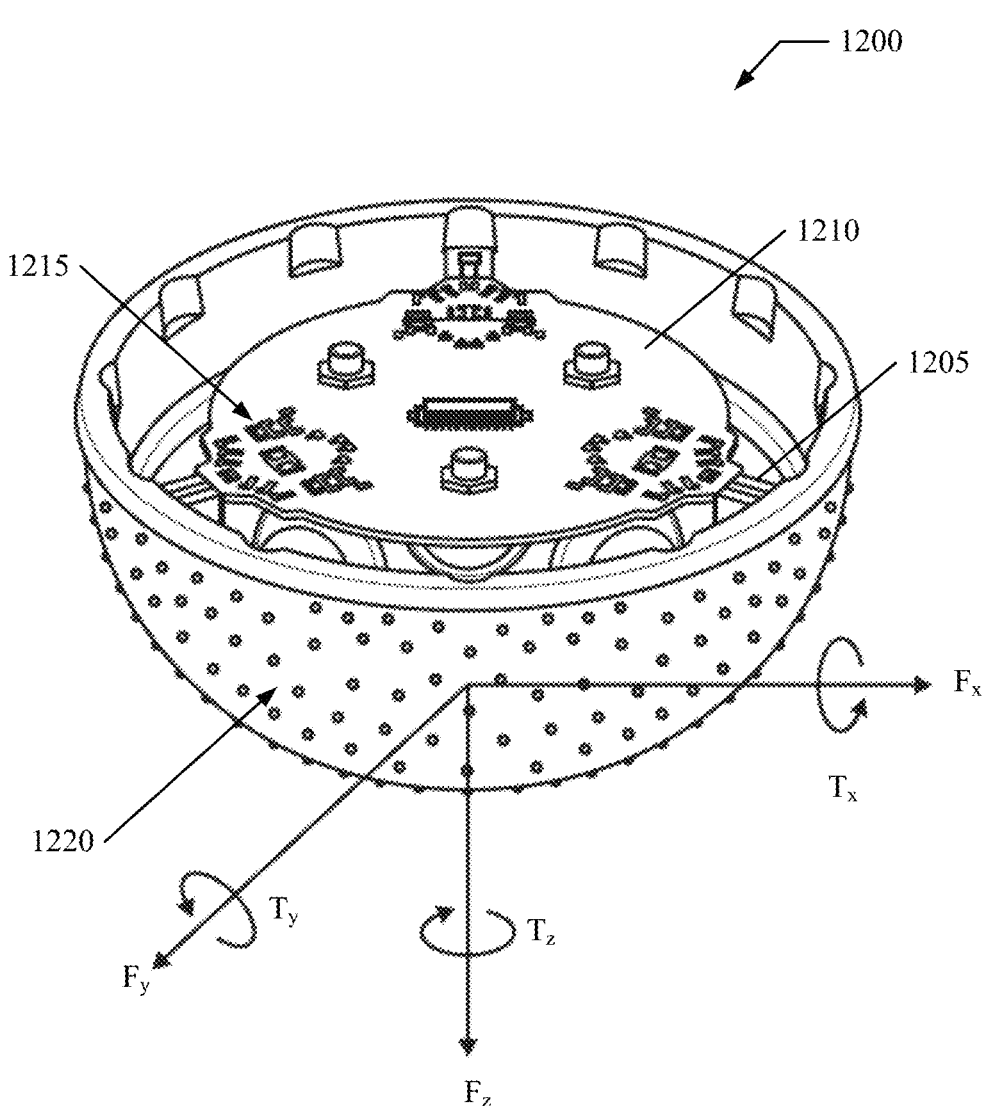
FIG. 12 illustrates an electronic signature system.

FIG. 12 illustrates an acetabular reamer/broach 1200, such as bone preparation implement 1110 illustrated in FIG. 11. Broach 1200 includes a set of sensing beams 1205 (e.g., transducers), an innerhall 1210, a low noise interface electronics interface 1215 for Ethernet, PCI, USB, EtherNet/IP, ProfiNet, and the like, an further includes an outer structure 1220 having a bone cutting/sensing structure.

Recent advances allow sensors to be directly integrated into desktop and laptop computers using off the shelf data-acquisition cards DAQ, which results in higher data speeds, easier installation, and flexibility in bus selection and operation systems.

A conventional sensor system includes a transducer, high flex cable, and a controller to convert strain gauge input to force and torque values. Output is sent to a computer using serial, analog or customized bus controller. Analog output is converted into digital format. Customized bus controllers can be expensive upgrades.

By contrast newer technology allows DAQ F/T sensors to work with many desktop and laptop computers on the market. The six-axis DAQ F/T sensor includes a transducer, high-flex cable, DAQ card, and software tools. Proprietary interface cards, on the market, placed on or near the transducer produce a low-noise seven channel signal that can be read by most off the shelf analog input DAQ cards with at least seven available channels. PC based software converts the single to force and torque output. The computer, through the DAQ card, powers the interface card and transducer. Bundled software includes a reusable, hardware-independent Windows ActiveX component that configures the transducer system and converts raw voltages into forces and torques. The system can be used in development platforms that support ActiveX or Automation containment, including Microsoft Visual Basic 6.0, Microsoft Visual C++, Microsoft.NET Platform, and National Instrument's LabVIEW, among others.

Figure 13:
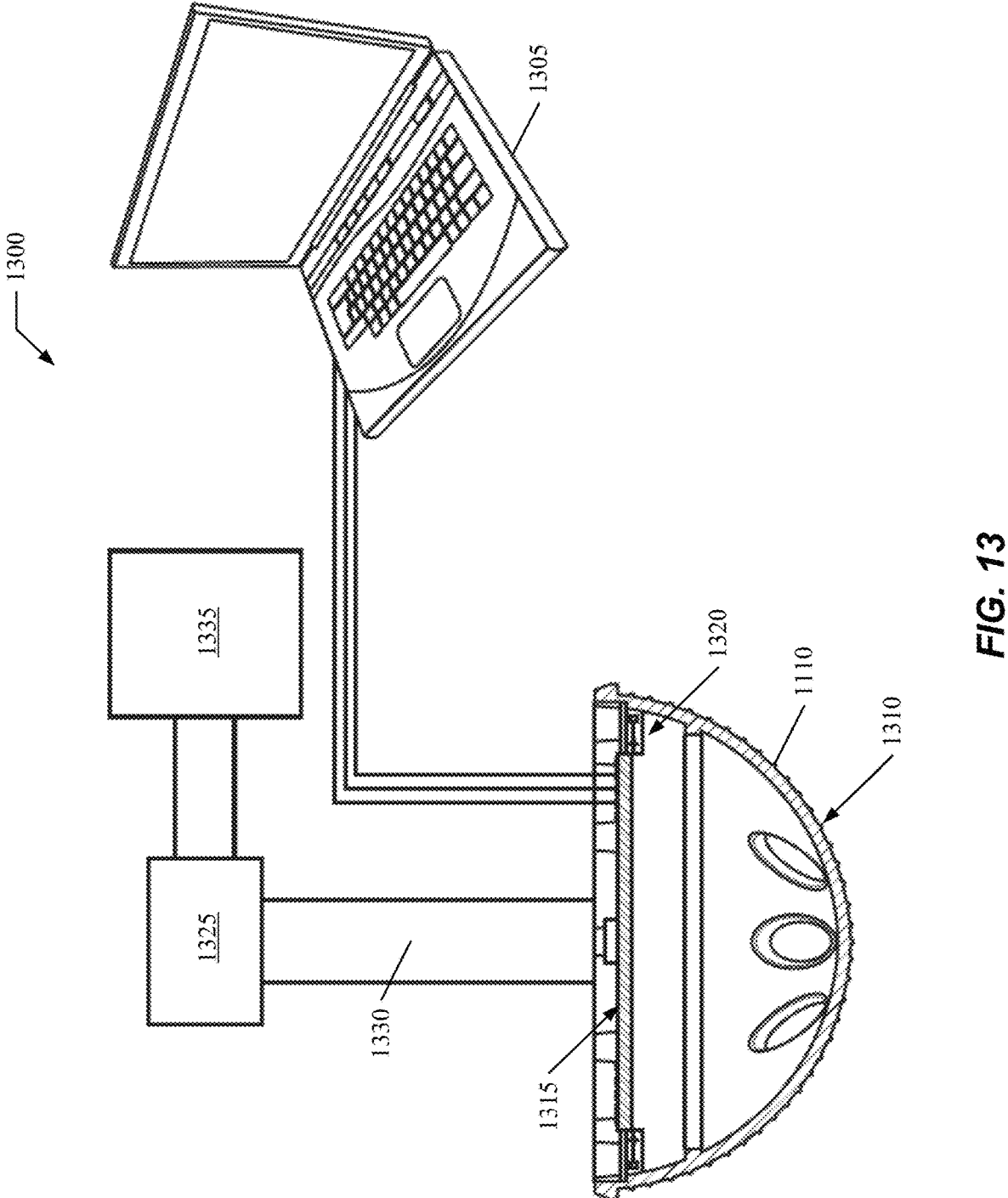
FIG. 13 illustrates an acetabular reamer/broach.

FIG. 13 illustrates an electronic signature system 1300. System 1300 includes a computing system 1305 (e.g., a laptop or other stored program computing platform having a processor, a memory from which instructions are obtained for operation on the processor, to effectuate the desired functions such as those described herein).

System 1300 further includes a bone preparation tool (e.g., acetabular reamer/broach 1110—broach 1200 or femoral broach 1115) having an outer bone cutting/sensing structure 1310, an innerhall 1315 with low noise interface electronics, and a set of sensing beams transducers 1320.

System 1300 further includes a driver 1325 (e.g., driver 1105 illustrated in FIG. 11) having a shaft 1330 coupled to the bone preparation tool 1110. Driver 1325 includes a motor and energy source (e.g., a battery) 1335.

F/T sensors also have valuable application in assembly of orthopedic implants into bone as well as assembly of modular orthopedic implants. The Force/Torque sensors can assemble the head on to the trunnion, in the modular assembly process, with a level of quantitative exactness that cannot be reproduced by humans. With this method surgeons can use robotic tools to assemble the femoral head unto the trunnion, with the robotic tool applying the exact how much force/torque required to produce a cold weld at the head/trunnion interface, preventing any type of metal debris, metalosis and trunnionosis.

Figure 14:
FIG. 14 illustrates a modular orthopedic implant.

FIG. 14 illustrates a modular orthopedic implant 1400. Implant 1400 includes a body 1405 (e.g, a femoral stem) having a trunnion 1410 and further includes a head 1415 (e.g., a femoral head) having a bore 1420 configured for mating with trunnion 1410.

F/T sensors also allow surgeons to have a sense of exactly how much force to apply to press fit the implants into bone. For example, the resistive frictional force at the rim of the acetabulum may be 4 KN. Surgeons may use up to 14 KN of force to impact (press fit) the acetabular cup into bone. A good portion of the extra 10 KNs of applied force is absorbed by the pelvis, frequently resulting in fractures, occult fractures, osteocyte death, and loss of vascularity. This system may allow the surgeon to know just the right amount of force to apply to overcome the resistive frictional forces at the rim of the bone cavity, thereby preventing excessive and unnecessary use of force, which injures patients.

The system and methods above has been described in general terms as an aid to understanding details of preferred embodiments of the present invention. In the description herein, numerous specific details are provided, such as examples of components and/or methods, to provide a thorough understanding of embodiments of the present invention. Some features and benefits of the present invention are realized in such modes and are not required in every case. One skilled in the relevant art will recognize, however, that an embodiment of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

Reference throughout this specification to "one embodiment", "an embodiment", or "a specific embodiment" means that a particular feature, structure, or characteristic described in connection with the embodiment is included in at least one embodiment of the present invention and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as part of the spirit and scope of the present invention.

It will also be appreciated that one or more of the elements depicted in the drawings/figures can also be implemented in a more separated or integrated manner, or even removed or rendered as inoperable in certain cases, as is useful in accordance with a particular application.

Additionally, any signal arrows in the drawings/Figures should be considered only as exemplary, and not limiting, unless otherwise specifically noted. Combinations of components or steps will also be considered as being noted, where terminology is foreseen as rendering the ability to separate or combine is unclear.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims. Thus, the scope of the invention is to be determined solely by the appended claims.

What is claimed as new and desired to be protected by Letters Patent of the United States is:

1. A bone processing apparatus for a processing of a cavity within a bone using a bone preparation tool, the cavity configured for a press fit fixation of a prosthesis within the cavity, comprising:
    a bone processing implement coupled to the bone preparation tool;
    a motor, coupled to the bone preparation tool, responsive to an input energy configured to process the cavity using said bone processing implement; and
    an energy signature system configured to provide a real time quantitative energy signature of the bone processing apparatus during the processing;
    wherein said energy signature system includes a power absorption mode configured to produce said real time quantitative energy signature responsive to an energy consumption of said motor during the processing.

2. The apparatus of claim 1 wherein said energy signature system includes a power transmission mode configured to coproduce said real time quantitative energy signature responsive to a measured force at a bone-implement interface during the processing.

3. A bone processing apparatus for a processing of a cavity within a bone using a bone preparation tool, the cavity configured for a press fit fixation of a prosthesis within the cavity, comprising:
    a bone processing implement coupled to the bone preparation tool;
    a motor, coupled to the bone preparation tool, responsive to an input energy configured to process the cavity using said bone processing implement; and
    an energy signature system configured to provide a real time quantitative energy signature of the bone processing apparatus during the processing;
    wherein said energy signature system includes a power transmission mode configured to produce said real time quantitative energy signature responsive to a measured force at a bone-implement interface during the processing.

4. The apparatus of claim 3 wherein said bone cutting implement includes a shaft coupled to said motor and further comprises a set of strain gauges estimating an angular deformation of said shaft during the processing, said set of strain gauges coupled to said shaft and wherein said real time quantitative energy signature is derived from said angular deformation.

5. The apparatus of claim 3 wherein said bone cutting implement includes a shaft coupled to said motor and further comprises a set of sensors estimating a bone-implement interface force during the processing; and wherein said real time quantitative energy signature is derived from said bone-implement interface force.

6. The apparatus of claim 5 wherein said set of sensors are selected from the group consisting of dynamometers, force/torque sensors, force gauges, and combinations thereof.

7. A bone processing apparatus for a processing of a cavity within a bone using a bone preparation tool, the cavity configured for a press fit fixation of a prosthesis within the cavity, comprising:

a bone processing implement coupled to the bone prepa-
ration tool;

a motor, coupled to the bone preparation tool, responsive
to an input energy configured to process the cavity
using said bone processing implement; and an energy signature system configured to provide a real
time quantitative energy signature of the bone process-
ing apparatus during the processing;

wherein the bone cavity includes a physical size, further
comprising a bone cavity size estimator configured to
produce a quantitative assessment of the physical size
during the processing and responsive to said real time
quantitative energy signature.

8. A bone processing apparatus for a processing of a
cavity within a bone using a bone preparation tool, the cavity
configured for a press fit fixation of a prosthesis within the
cavity, comprising:

a bone processing implement coupled to the bone prepa-
ration tool;

a motor, coupled to the bone preparation tool, responsive
to an input energy configured to process the cavity
using said bone processing implement; and an energy signature system configured to provide a real
time quantitative energy signature of the bone process-
ing apparatus during the processing;

wherein the bone includes an elastic limit, further com-
prising a bone elastic limit estimator configured to
produce a quantitative assessment of the elastic limit
during the processing and responsive to said real time
quantitative energy signature.

* * * * *